US00PP25692P2

(12) United States Plant Patent
Princen et al.

(10) Patent No.: US PP25,692 P2
(45) Date of Patent: Jul. 14, 2015

(54) APPLE TREE NAMED 'WILTONS STAR'

(50) Latin Name: *Malus domestica*
Varietal Denomination: Wiltons Star

(71) Applicants: Wilhelmus Johannes Franciscus Antonius Princen, Weert (NL); Antonius Franciscus Marie Johannes Princen, Weert (NL)

(72) Inventors: Wilhelmus Johannes Franciscus Antonius Princen, Weert (NL); Antonius Franciscus Marie Johannes Princen, Weert (NL)

(73) Assignee: Prince International S.A.R.L., Luxembourg (LU)

( * ) Notice: Subject to any disclaimer, the term of this patent is extended or adjusted under 35 U.S.C. 154(b) by 56 days.

(21) Appl. No.: 13/815,876

(22) Filed: Mar. 15, 2013

(51) Int. Cl.
*A01H 5/00* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell
(74) *Attorney, Agent, or Firm* — C. A. Whealy

(57) ABSTRACT

A new and distinct cultivar of Apple tree named 'Wiltons Star', characterized by its upright plant habit; above average fruit production; and fruits with smooth, dark red-colored skin.

4 Drawing Sheets

Botanical designation: *Malus domestica.*
Cultivar denomination: 'WILTONS STAR'.

BACKGROUND OF THE INVENTION

The present invention relates to a new and distinct cultivar of Apple tree, botanically known as *Malus domestica* and hereinafter referred to by the name 'Wiltons Star'.

The new Apple tree is a naturally-occurring whole plant mutation of *Malus domestica* 'Red Jonaprince', disclosed in U.S. Plant Pat. No. 11,112. The new Apple tree was discovered and selected by the Inventors from within a population of fruiting trees of 'Red Jonaprince' during the summer of 1998 in an outdoor orchard in Weert, The Netherlands.

Asexual reproduction of the new Apple tree by grafting since February, 1999 in a controlled environment in Weert, The Netherlands has shown that the unique features of this new Apple tree are stable and reproduced true to type in successive generations.

SUMMARY OF THE INVENTION

The new Apple tree has not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Wiltons Star'. These characteristics in combination distinguish 'Wiltons Star' as a new and distinct Apple tree:

1. Upright plant habit.
2. Above average fruit production.
3. Fruits with smooth, dark red-colored skin.

The new Apple tree differs primarily from plants of the parent, 'Red Jonaprince', in fruit skin appearance as fruits of the new Apple tree have smaller and less noticeable lenticels than fruits of trees of 'Red Jonaprince' which have prominent lenticels giving the fruits a spotted appearance.

Plants of the new *Malus* can be compared to plants of *Malus domestica* 'Jonagold', not patented. In side-by-side comparisons conducted in Weert, The Netherlands, the new Apple tree differed primarily from trees of 'Jonagold' in the following characteristics:

1. Fruits of the new Apple tree developed color two to three weeks earlier than fruits of trees of 'Jonagold'.
2. Fruits of the new Apple tree were solid dark red in color without noticeable spots (lenticels) and color streaks (color breaks) whereas fruits of trees of 'Jonagold' had prominent lenticels and were striped.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet comprises a side perspective view of a typical tree of 'Wiltons Star' grown in an outdoor orchard.

The photograph on the second sheet is a close-up view of a typical tree of 'Wiltons Star' grown in an outdoor orchard.

The photograph on the third sheet is a close-up view of a typical fully-developed fruit of 'Wiltons Star'.

The photograph on the fourth sheet is a close-up view of a typical flower of 'Wiltons Star'.

DETAILED BOTANICAL DESCRIPTION

The aforementioned photographs, following observations and measurements describe plants grown during the summer in Weert, The Netherlands in an outdoor orchard and under cultural conditions and practices typical of commercial Apple tree production. Plants were four years old when the photographs and description were taken. Measurements and numerical values represent averages for typical plants and plant parts. The actual measurements of any individual plant or plant parts, or any group of plants or plant parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* 'Wiltons Star'.

Parentage: Naturally-occurring whole plant mutation of *Malus domestica* 'Red Jonaprince', disclosed in U.S. Plant Pat. No. 11,112.

Propagation:

*Type*.—By grafting.

*Time to initiate roots, summer*.—About eight weeks at 24° C.

*Time to initiate roots, winter*.—About 16 weeks at 24° C.

*Time to produce a rooted young plant, summer*.—About five months at 24° C.

*Time to produce a rooted young plant, winter*.—About eight to ten months at 24° C.

*Root description*.—Fibrous, woody; brown in color.

*Rooting habit*.—Moderate branching; medium density.

Plant description:

*Plant and growth habit*.—Upright plant habit and moderately vigorous growth habit.

*Tree height*.—About three meters.

*Tree diameter*.—About 80 cm to 100 cm.

*Trunk description*.—Diameter: About 4 cm to 6 cm. Strength: Strong. Texture: Woody. Color: Close to 200A.

*Lateral branch description*.—Length: About 50 cm to 70 cm. Diameter: About 2.5 cm to 3 cm. Internode length: About 2 cm to 3 cm. Texture: Smooth, glabrous. Angle of attachment: About 10° from main branch axis. Strength: Strong. Color: Close to 200A.

*Leaf description*.—Arrangement: Alternate; simple. Length: About 10.5 cm. Width: About 7.5 cm. Shape: Ovate. Apex: Acute. Base: Cordate. Margin: Serrate. Texture, upper surface: Smooth, glabrous. Texture, lower surface: Rough, pubescent. Venation pattern: Pinnate. Color: Developing and fully developed leaves, upper surface: Close to 147A; venation, close to 147D. Developing and fully developed leaves, lower surface: Close to 147B; venation, close to 145D. Petiole: Length: About 1 cm to 3 cm. Diameter: About 5 mm. Texture, upper and lower surfaces: Smooth, glabrous. Color, upper and lower surfaces: Close to 138A.

Flower description:

*Flower type and flowering habit*.—Numerous single rotate flowers arranged on compound panicles; flowers face mostly outward to drooping.

*Fragrance*.—Faint, pleasant.

*Natural flowering season*.—Continuously flowering in April and May in The Netherlands.

*Inflorescence height*.—About 4 cm to 6 cm.

*Inflorescence diameter*.—About 4 cm to 6 cm.

*Quantity of flowers per inflorescence*.—About six to ten.

*Flower diameter*.—About 2 cm to 3 cm.

*Flower depth* (*height*).—About 5 mm to 10 mm.

*Flower longevity on plant*.—About two weeks; flowers not persistent.

*Flower buds*.—Shape: Oval to rounded. Length: About 1 cm to 2 cm. Diameter: About 5 mm to 10 mm. Color: White to light pink, close to N155B and to 63B to 63C.

*Petals*.—Quantity and arrangement: Typically five in a single whorl; slightly imbricate. Length: About 1 cm to 1.5 cm. Width: About 5 mm to 8 mm. Shape: Obovate to elliptic. Apex: Obtuse. Base: Cordate. Margin: Entire; slightly undulate. Texture, upper and lower surfaces: Smooth, glabrous; satiny. Color: When opening and fully opened, upper surface: Close to 155D; tinged with light pink, close to 63C, towards the apex. When opening and fully opened, lower surface: Close to 155D.

*Sepals*.—Quantity and arrangement: Typically five in a single whorl. Length: About 4 mm to 6 mm. Width: About 3 mm to 5 mm. Shape: Ovate to somewhat deltoid. Apex: Rounded. Base: Cordate. Margin: Entire. Texture, upper and lower surfaces: Smooth, glabrous. Color, upper and lower surfaces: Reddish green, close to 147B to 147C, slightly overlain with close to 187A.

*Pedicels*.—Length: About 3 cm to 5 cm. Diameter: About 1 mm to 2 mm. Strength: Moderately strong. Aspect: About 60° to 90° from stem. Texture: Smooth, glabrous. Color: Greyish green tinged with light, red, close to 194A and 178D.

*Reproductive organs*.—Stamens: Quantity: About 20 per flower. Filament length: About 1 cm. Filament color: Close to 155D. Anther length: About 3 mm to 5 mm. Anther shape: Reniform, bi-lobed. Anther color: Close to 158A. Pollen amount: Scarce. Pollen color: Close to 158A. Pistils: Quantity: About five to seven per flower. Pistil length: About 1 cm. Stigma color: Light green. Style length: Less than 1 cm. Style color: Greenish white.

Fruit description:

*Ripening time*.—Typically early September in The Netherlands.

*Yield*.—Moderately heavy.

*Use*.—Fresh.

*Length*.—About 6.5 cm to 7 cm.

*Diameter*.—About 7.5 cm to 8.5 cm.

*Fruit weight*.—Typically individual fruits will weigh between 190 to 250 grams depending on environmental conditions. General shape in profile Globose.

*Depth of eye basin*.—Medium, about 8.8 mm.

*Width of eye basin*.—Medium, about 3.1 cm.

*Fruit stalk diameter*.—About 1 mm.

*Fruit stalk color*.—Reddish brown, close to 178A.

*Fruit skin color*.—Ground color, close to 160B, overlain with close to 46A; red color solid without streaks or stripes.

*Lenticels*.—Not prominent. Length: About 1 to 2 mm. Density: About six per square inch. Color: Close to 162A.

*Flesh texture*.—Crisp, firm

*Flesh color*.—Yellowish cream, close to between 4D and 158B.

*Flavor*.—Rich, aromatic.

*Locules*.—Quantity per fruit: About five. Length: About 1.5 cm to 2.5 cm. Width: About 5 mm to 10 mm. Shape: Elliptic to ovate.

*Seeds*.—Quantity per locule: None to about four depending on environmental conditions. Length: About 5 mm. Diameter: About 3 mm. Shape: Elongated conical. Color: Brown.

Temperature tolerance: The new Apple tree has been observed to tolerate temperatures ranging from about −20° C. to about 35° C.

It is claimed:

1. A new and distinct Apple tree named 'Wiltons Star' as illustrated and described.

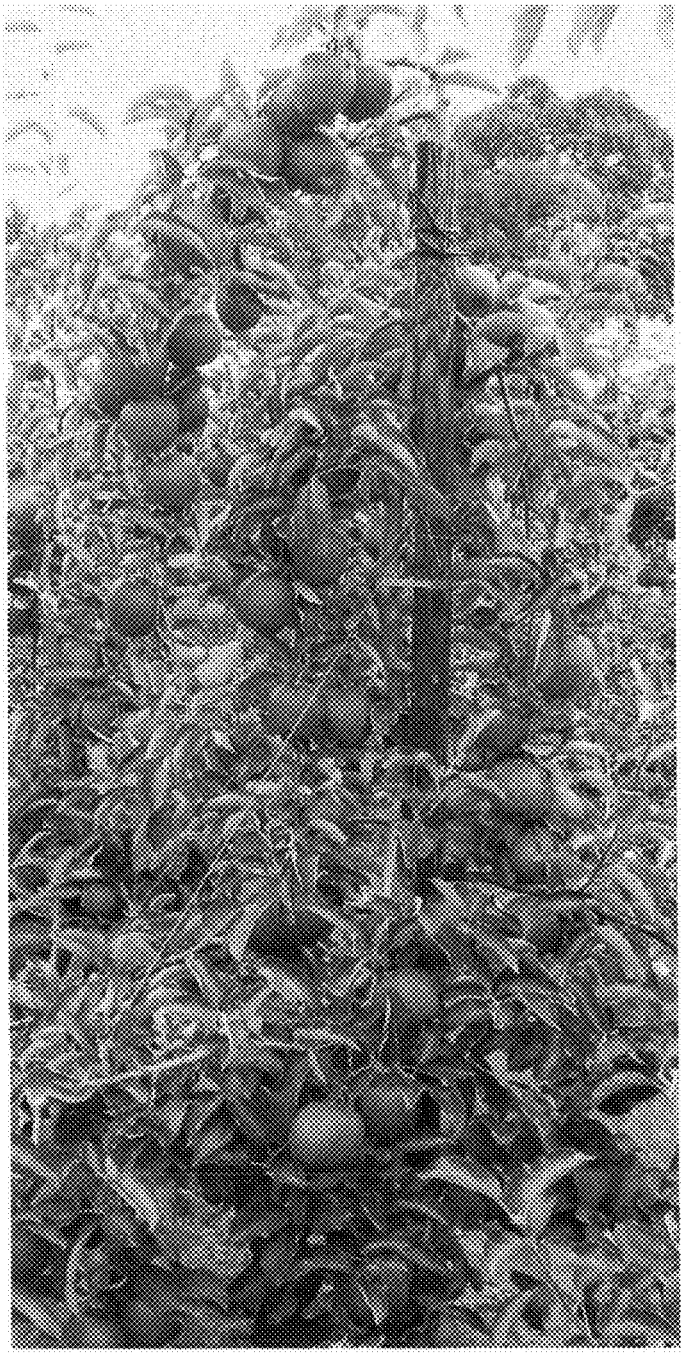

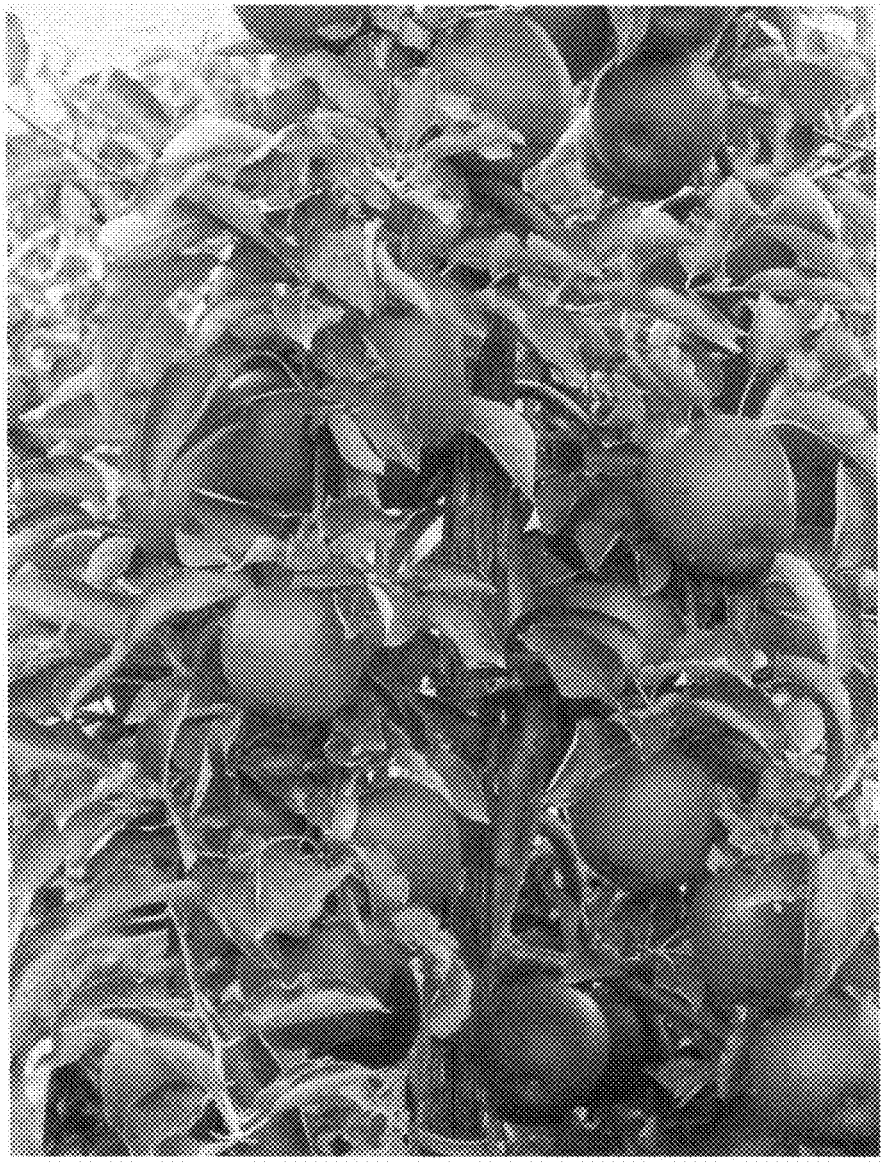

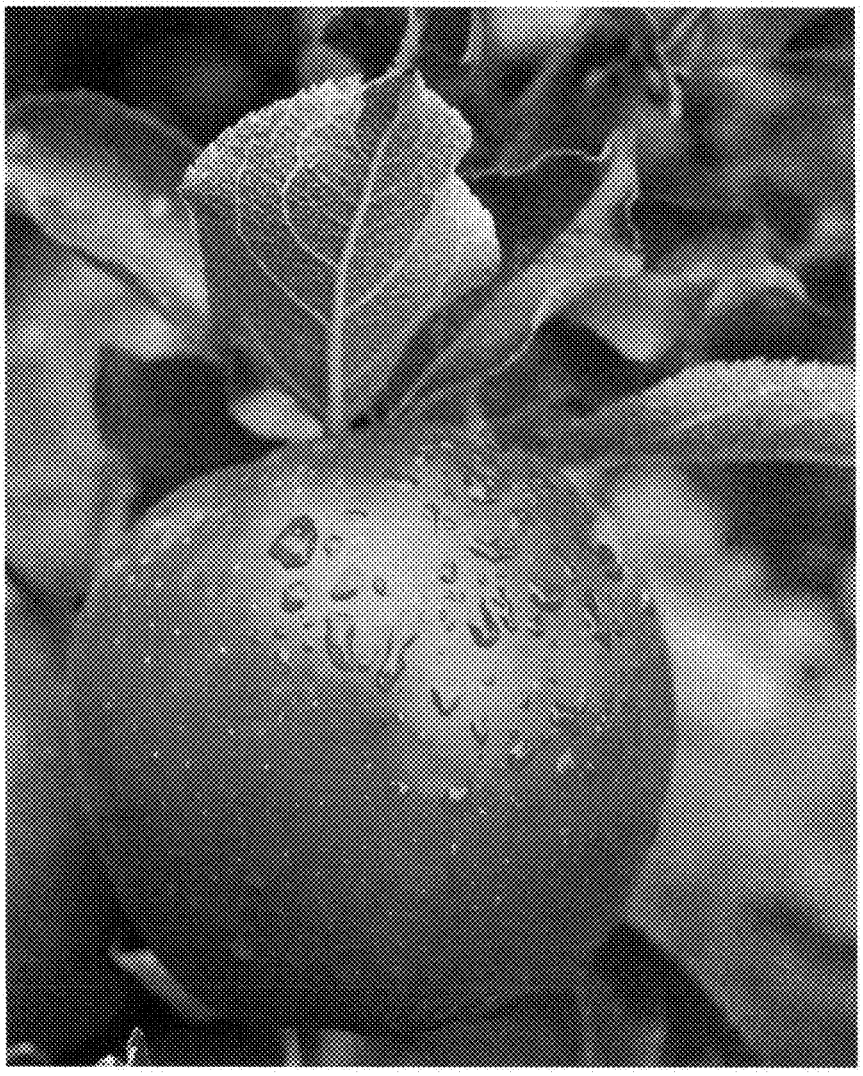

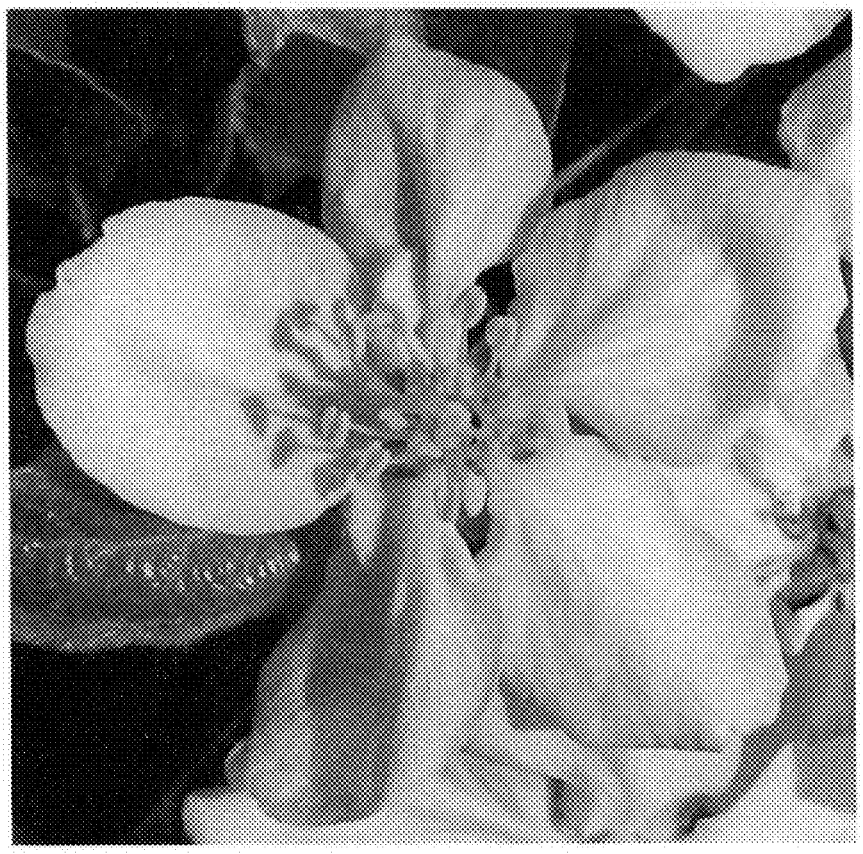

* * * * *